United States Patent
Gouda et al.

(10) Patent No.: US 12,246,099 B1
(45) Date of Patent: Mar. 11, 2025

(54) WOUND DRESSING BASED ON POLYMERIC MIXTURE OF CELLULOSE ACETATE AND HYALURONIC ACID EMBEDDED WITH COPPER OXIDE AND MAGNESIUM OXIDE NANOPARTICLES

(71) Applicant: King Faisal University, Al-Ahsa (SA)

(72) Inventors: Mohamed Gouda, Al-Ahsa (SA); Hany Mohamed Abd El-Lateef Ahmed, Al-Ahsa (SA)

(73) Assignee: KING FAISAL UNVERSITY, Al-Ahsa (SA)

( * ) Notice: Subject to any disclaimer, the term of this patent is extended or adjusted under 35 U.S.C. 154(b) by 0 days.

(21) Appl. No.: 18/533,052

(22) Filed: Dec. 7, 2023

Related U.S. Application Data (62) Division of application No. 18/244,012, filed on Sep. 8, 2023.

(51) Int. Cl.
*A61L 15/18* (2006.01)
*A61L 15/28* (2006.01)

(52) U.S. Cl.
CPC ............... *A61L 15/28* (2013.01); *A61L 15/18* (2013.01); *A61L 2400/12* (2013.01)

(58) Field of Classification Search
CPC ............................. A61L 15/28; A61L 2400/12
See application file for complete search history.

(56) References Cited

U.S. PATENT DOCUMENTS

| | | | |
|---|---|---|---|
| 10,130,521 B2 * | 11/2018 | Junginger | A61F 13/00991 |
| 10,995,010 B1 | 5/2021 | Aldalbahi et al. | |
| 2004/0001879 A1 * | 1/2004 | Guo | C08L 1/04 424/445 |
| 2016/0250378 A1 * | 9/2016 | Freer | A61K 9/0014 424/489 |
| 2018/0147177 A1 | 7/2018 | Bastos et al. | |

FOREIGN PATENT DOCUMENTS

| | | | |
|---|---|---|---|
| CN | 112426565 A | 3/2021 | |
| RU | 2766223 C1 * | 2/2022 | |
| WO | WO-2016161176 A1 * | 10/2016 | A61K 31/506 |

OTHER PUBLICATIONS

RU 2766223 C1 Machine Translation (Year: 2022).*
Borkow, Gadi, Neta Okon-Levy, and Jeffrey Gabbay. "Copper oxide impregnated wound dressing: biocidal and safety studies." Wounds 22.12 (2010): 301-310.
Taher, Fatemah A., et al. "Magnesium Ortho-Vanadate/Magnesium Oxide/Graphene Oxide Embedded through Cellulose Acetate-Based Films for Wound Healing Applications." Materials 16.8 (2023): 3009.
Wang, Fei, et al. "Improved antimicrobial ability of dressings containing berberine loaded cellulose acetate/hyaluronic acid electrospun fibers for cutaneous wound healing." Journal of Biomedical Nanotechnology 18.1 (2022): 77-86.

* cited by examiner

*Primary Examiner* — Sarah Pihonak
*Assistant Examiner* — Mikhail O'Donnel Robinson
(74) *Attorney, Agent, or Firm* — Nath, Goldberg & Meyer; Joshua B. Goldberg (57) ABSTRACT

Wound dressings fabricated from a polymeric mixture of cellulose acetate and hyaluronic acid embedded with copper oxide and/or magnesium oxide nanoparticles and a method of making the wound dressing. The method includes combining hyaluronic acid and deionized water to form a first mixture, combining cellulose acetate and acetone to form a second mixture, combining the first and second mixtures to form a third mixture of hyaluronic acid, cellulose acetate, deionized water and acetone, separately adding at least one of a copper acetate solution and a magnesium chloride solution to the third mixture to form a fourth mixture, adding sodium hydride to the fourth mixture to form a final mixture, and drying the final mixture to form a film used for the wound dressing. Different weights of copper oxide and magnesium oxide can be chosen to achieve a certain morphological appearance. The wound dressing is a promising option for wound healing.

4 Claims, 9 Drawing Sheets

WOUND DRESSING BASED ON POLYMERIC MIXTURE OF CELLULOSE ACETATE AND HYALURONIC ACID EMBEDDED WITH COPPER OXIDE AND MAGNESIUM OXIDE NANOPARTICLES

CROSS-REFERENCE TO RELATED APPLICATION

This application is a divisional of U.S. patent application Ser. No. 18/244,012, filed on Sep. 8, 2023, the entire contents of which are incorporated herein by reference.

BACKGROUND

Field

The disclosure of the present patent application relates to wound dressings, and particularly to a wound dressing based on a polymeric mixture of cellulose acetate and hyaluronic acid with embedded copper oxide and magnesium oxide nanoparticles.

Description of Related Art

Numerous injuries, and particularly burns, require the application of some type of pad, gauze, cloth, dressing, or similar covering (herein collectively called a "dressing") to protect the wound while it is healing. Wounds, especially burns, sometimes have difficulty in healing and are frequently prone to infection because natural protective skin barriers are disrupted and are slow in repairing themselves. The most commonly used dressing material has been cotton because it is both inexpensive and readily available. However, as those who have used cotton dressings are aware, they tend to stick to the injured area, even when the surface of the area is covered with a lubricant such as petroleum jelly ("petrolatum") or similar substance, or a medicinal agent which contains a lubricant.

Developments in the medical arts have resulted in some improvements in medical dressings, two of which are represented by Johnson & Johnson's ADAPCTIC™ brand non-adherent dressings and the Curity® brand TELFA® sterile pads sold by Kendall-Futuro Company. The ADAPTIC™ brand dressing was found to consist of a cellulose acetate pad which has been soaked in petrolatum or similar substance to impart anti-adhesion properties. While the petrolatum reduces adhesion to a wound, it's use results in a pad that is greasy and messy to handle compared to a pad without petrolatum. The TELFA® dressing consists of a polyethylene terephthalate (PET) shell and a caustic washed cotton insert, the anti-adhesion properties being imparted by the PET shell.

Current dressings, while having various qualities which may reduce adhesion or provide other benefits, typically incorporate lubricants and/or fluids or fluid releasing agents and use fibers other than cellulose acetate to provide non-adhesion properties.

While certain current dressings represent improvements in reducing dressing adhesion to wounds, further improvements in the field are highly desirous. Thus, new wound dressings solving the aforementioned problems are desired.

SUMMARY OF THE INVENTION

An improved dressing of cellulose acetate and hyaluronic acid would be useful in the medical arts. Cellulose acetate is both chemotactic for attracting white blood cells and hydrophilic. The white cell chemotactic property of cellulose acetate fibers is desirable in a wound dressing because white blood cells aid in fighting infection. The hydrophilic property is desirable because it aids in removing excess fluids which may ooze from the surface of a wound during the healing process. Hyaluronic acid helps skin stretch and flex and reduces skin wrinkles and lines. Hyaluronic acid is also proven to help wounds heal faster and can reduce scarring.

Accordingly, the present subject matter relates to wound dressings fabricated from a polymeric mixture of cellulose acetate (CA) and hyaluronic acid (HA) embedded with copper oxide and/or magnesium oxide (MgO) nanoparticles. In particular, the present wound dressing includes a polymeric mixture of cellulose acetate and hyaluronic acid as well as nanoparticles embedded in the polymeric mixture, the nanoparticles being selected among copper oxide nanoparticles, magnesium oxide nanoparticles, and combinations thereof. Different weights of these substances can be chosen during manufacture to achieve a certain morphological appearance. The multifunctional wound dressing could be a promising and potential option for wound healing.

In an embodiment, the present subject matter relates to a method of making a wound dressing, the method including combining hyaluronic acid and deionized water to form a first mixture, combining cellulose acetate and acetone to form a second mixture, and combining the first and second mixtures to form a third mixture of hyaluronic acid, cellulose acetate, deionized water, and acetone. The method further includes separately adding at least one of a copper acetate solution and a magnesium chloride solution to the third mixture to form a fourth mixture and adding sodium hydride to the fourth mixture under an ultrasonic bath to form a final mixture. The final mixture is dried to form a film used for the wound dressing.

In a further embodiment, the present subject matter relates to a method of healing a wound in a patient comprising applying to a patient in need thereof a wound dressing as described herein at a site of the wound in the patient.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as wound healinjn y54ng.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a wound dressing comprising a polymeric mixture comprising: cellulose acetate and hyaluronic acid; and nanoparticles embedded in the polymeric mixture. The nanoparticles can be selected from the group consisting of copper oxide nanoparticles, magnesium oxide nanoparticles, and combinations thereof.

In one embodiment of the present wound dressings, the nanoparticles can be the copper oxide nanoparticles. In another embodiment of the present wound dressings, the nanoparticles can be the magnesium oxide nanoparticles. In yet another embodiment of the present wound dressings, the nanoparticles can be a combination of the copper oxide nanoparticles and the magnesium oxide nanoparticles.

In a further embodiment, the nanoparticles can be evenly distributed throughout the polymeric mixture.

In an additional embodiment, the combination of the copper oxide nanoparticles and the magnesium oxide nanoparticles can prevent degradation of the wound dressing.

In another embodiment, the present subject matter relates to a method for making a wound dressing, the method comprising: combining hyaluronic acid and deionized water to form a first mixture; combining cellulose acetate and acetone to form a second mixture; combining the first and second mixtures to form a third mixture of hyaluronic acid, cellulose acetate, deionized water and acetone; separately adding at least one of a copper acetate solution and a magnesium chloride solution to the third mixture to form a fourth mixture; adding sodium hydride to the fourth mixture under an ultrasonic bath to form a final mixture; and drying the final mixture to form a film used for the wound dressing.

In certain embodiments in this regard, the ratio of hyaluronic acid to deionized water in the first mixture can be about 1:10 (m/v) (g/mL), the ratio of cellulose acetate to acetone in the second mixture can be about 1:10 (m/v) (g/mL), and/or the ultrasonic bath used to form a final mixture lasts for a minimum of 30 minutes.

In other embodiment, the third mixture can be stirred until a clear solution is obtained.

In an additional embodiment, both the copper acetate solution and the magnesium chloride solution can be added to the third mixture to form the fourth mixture.

In a further embodiment, the present subject matter relates to a method of healing a wound in a patient comprising applying to a patient in need thereof a wound dressing as described herein at a site of the wound in the patient.

In certain embodiments in this regard, the wound dressing includes the copper oxide nanoparticles. In other embodiments, the wound dressing includes the magnesium oxide nanoparticles. In yet other embodiments, the wound dressing includes the copper oxide nanoparticles and the magnesium oxide nanoparticles.

In an embodiment, the application of the wound dressing to the site of the wound in the patient can encourage cell growth at the site of the wound of the patient. Similarly, in another embodiment, the application of the wound dressing to the site of the wound can expedite healing of the wound of the patient.

The following examples relate to various methods of manufacturing certain specific wound dressings, and experimental results of the wound dressings described herein.

EXAMPLES

The materials used for the experiments were acquired from Sigma-Aldrich, including Cellulose acetate (Mn~50.000 by GPC) and hyaluronic acid, as well as $MgCl_2$ and copper acetate. All of the chemical reagents used in the experiment were of analytical quality and were employed right away without further purification.

Example 1

Fabrication of HA/CA Film Containing Metal Oxide Nanoparticles

In a flask with stirring, deionized water (100 mL) and hyaluronic acid (HA, 10 g) were combined. Once the hyaluronic acid had completely dissolved, 10 g of cellulose acetate in 100 mL of acetone (10%, or 1:10 m/v) was added with vigorously stirring using a mechanical stirrer to obtain a clear solution mixture of cellulose acetate and hyaluronic acid (CA/HA). Next, 0.1M of copper acetate and magnesium chloride solution was added separately to the prepared polymeric mixture solution (CA/HA). Next, 0.05M of sodium hydride as a reducing agent was added under an ultrasonic bath for 30 min. The film samples were then cast in a Petri dish and left in a drier furnace until fully dried. Seven film samples were prepared during experimental testing as follows: pure cellulose acetate (CA), pure hyaluronic acid (HA), copper oxide and cellulose acetate (CuO@CA), magnesium oxide and cellulose acetate (MgO@CA), copper oxide and hyaluronic acid (CuO@HA), magnesium oxide and hyaluronic acid (MgO@HA), and copper oxide-magnesium oxide and cellulose acetate/hyaluronic acid (CuO—MgO@CA/HA) were prepared.

Example 2

Analysis of HA/CA Film Containing Metal Oxide Nanoparticles

Experiments were conducted to fabricate wound dressings with desirable features such as bioactivity, biocompatibility, and non-toxicity in order to fast-track the healing process of a wound. Polymeric mixtures were fabricated from cellulose acetate (CA) and hyaluronic acid (HA) embedded with copper oxide and magnesium oxide (MgO) nanoparticles as a scaffold in wound healing applications. Several methods, including X-ray powder diffraction (XRD), contact angle, Fourier-transform infrared spectroscopy (FTIR), and SEM (scanning electron microscope) spectroscopy, were employed to characterize the structural and morphological characteristics of prepared nanocomposite samples. The data obtained from SEM analysis revealed a clean surface of polymer formation with appearance of nanoparticles of rough size and distribution in regions of varied densities through addition of binary metal oxide nanoparticles (CuO/MgO@HA/CA). XRD diffraction patterns revealed a strong crystallinity which represents CuO nanoparticles and the polycrystalline cubic structure of MgO nanoparticles.

Swelling rate percent, contact angle and the degradation behavior studies showed that the swelling rate percent of the polymer mixture film decreased when adding nanometal oxides. Regarding the contact angle, it was increased by incorporating the metal oxide nanoparticles in the polymeric mixture structure. Contact angles were 300 for hyaluronic acid (HA), 430 for MgO@HA/CA, 450 for CuO/MgO@HA/CA, 470 for CuO@HA/CA, and 620 for cellulose acetate.

The degradation behavior of prepared samples showed that all the samples immersed in phosphate-buffered saline (PBS) solution saw the fastest rate of deterioration after the first 3 days, while CA and CuO/MgO@HA/CA samples exhibit lower rates of deterioration and the sample containing a mixture of metal oxide nanoparticles (CuO/MgO@HA/CA) exhibited a lower weight loss value when compared to HA, HA/CA, and CA samples. Human osteosarcoma MG-63 cells were used in in-vitro cytotoxicity tests. CuO/MgO@HA/CA sample treatment on the cells suggests a non-cytotoxic impact, in contrast to the MTT test, which yields cell viability values of between 70% and 80% (after 72 h).

XRD

Figure 1A:
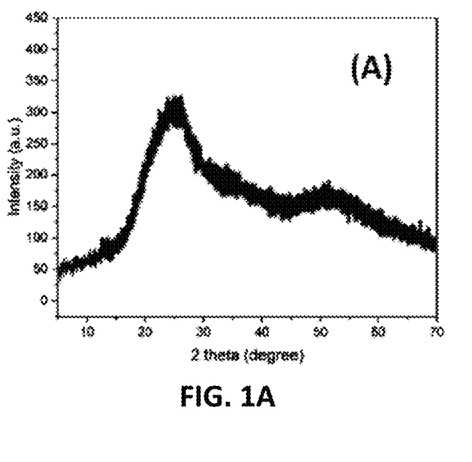
FIGS. 1A-1G show XRD patterns of various materials, including cellulose acetate (CA) (FIG. 1A), hyaluronic acid (HA) (FIG. 1B), hyaluronic acid with embedded magnesium oxide nanoparticles (MgO@HA) (FIG. 1c), hyaluronic acid with embedded copper oxide nanoparticles (CuO@HA) (FIG. 1D), cellulose acetate with embedded copper oxide nanoparticles (CuO@CA) (FIG. 1E), cellulose acetate with embedded magnesium oxide nanoparticles (MgO@CA) (FIG. 1F), and a polymeric matrix of cellulose acetate and hyaluronic acid with embedded magnesium oxide and copper oxide nanoparticles (CuO/MgO@HA/CA) (FIG. 1G).
Figure 1B:
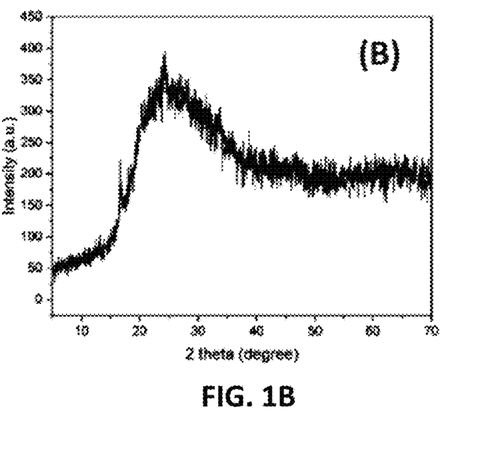
Figure 1C:
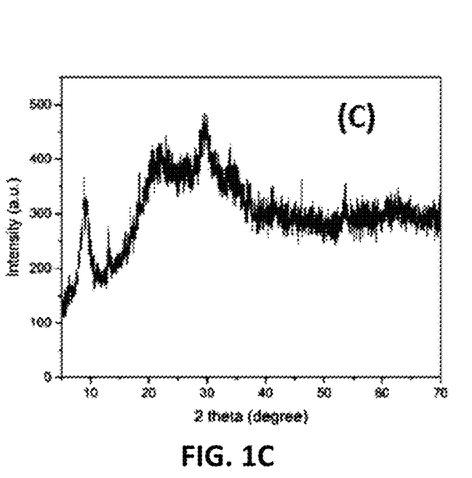
Figure 1D:
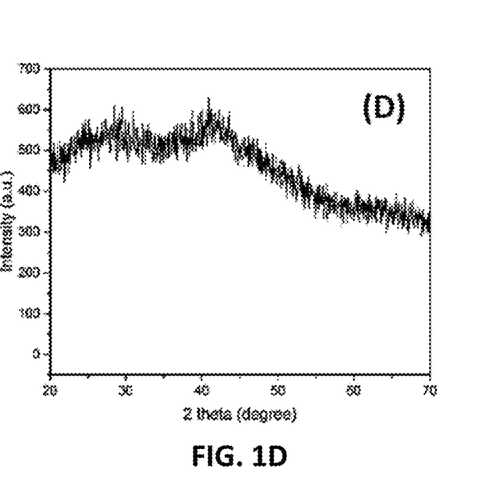
Figure 1E:
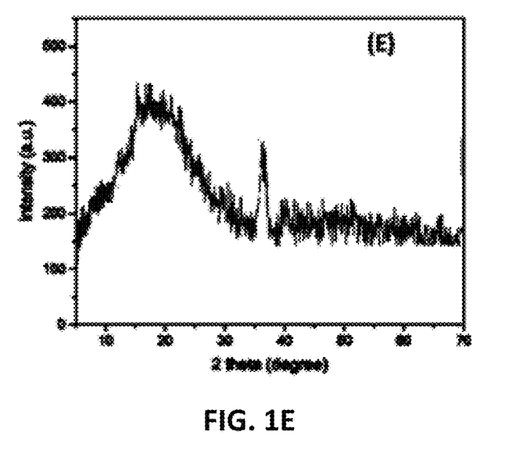
Figure 1F:
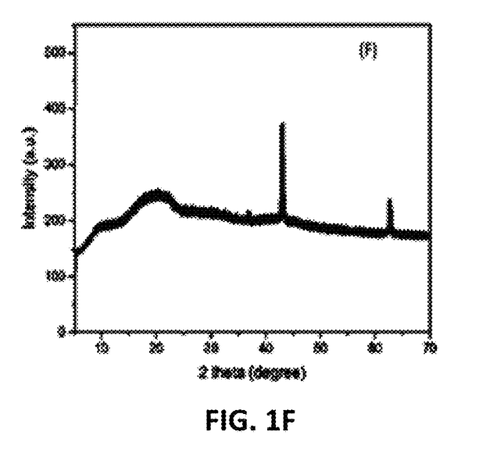
Figure 1G:
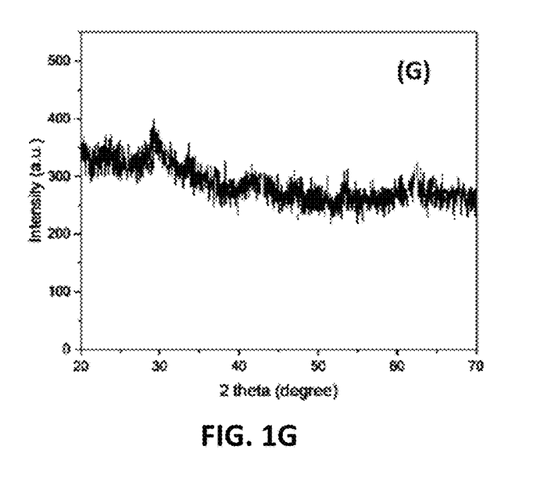

FIG. 1A shows the diffraction spectrum of pure cellulose acetate represents the different broad halo peak in the range of 20 at 15-30, coming from the amorphous nature of cellulose acetate. FIG. 1B represents the XRD pattern of pure hyaluronic acid which displays that the diffraction peaks at 2θ=20.8°, 46.7°, and 63.2°. FIG. 1E shows the XRD pattern of the CuO@CA nanocomposites, revealing the presence of a sharp crystalline peak at 2θ, 36°, which represents the presence of the copper oxide nanomaterial in the nanocomposite. FIG. 1F shows the typical cubic magnesium oxide peaks in the MgO@CA film diffractogram at 2θ=43.1 and 62.5. FIG. 1G displays the diffraction pattern of the CuO/MgO@HA/CA film, showing strong crystallinity since its diffraction peaks are stated at 2θ=8.8°, 13.01°, 29.6°, and 53.5° which represents copper oxide nanoparticles and the polycrystalline cubic structure of magnesium oxide nanoparticles exhibit several peaks at 2θ=29.4°, 310, 38.7°, 42.2°, and 63°.

FTIR

Figure 2A:
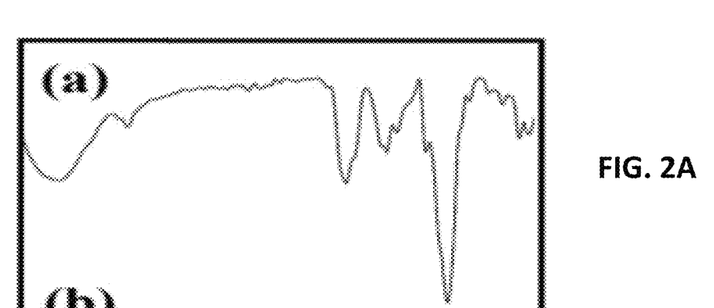
FIGS. 2A-2C show FTIR Spectra for HA (FIG. 2A), CA (FIG. 2B), and CuO/MgO@HA/CA (FIG. 2C).
Figure 2B:
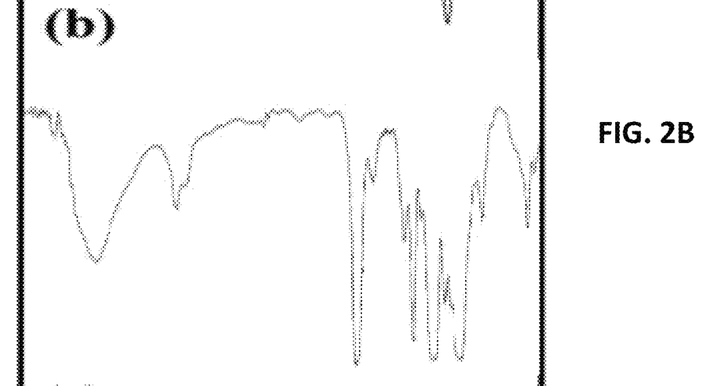
Figure 2C:
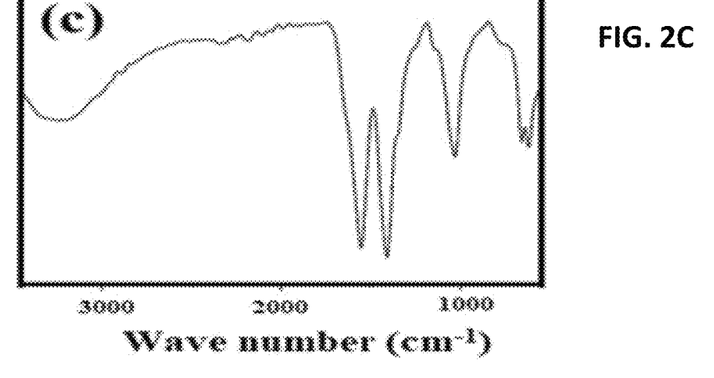

FIG. 2A shows the structural bands at 1025 $cm^{-1}$, 1155 $cm^{-1}$, and 1377 $cm^{-1}$ in the pure HA spectra show C—O—C symmetry, aliphatic ether C—O stretching, and amino acid carboxyl groups, respectively. Also included are references to symmetrical C—O stretching, asymmetric C=O, C—H stretching vibrations, and hydrogen-bonded hydroxyl (OH) groups in the mid-intensity bands shown at 1408 $cm^{-1}$, 1613 $cm^{-1}$, 2889 $cm^{-1}$, and 3319 $cm^{-1}$. FIG. 2B represents the FTIR spectral analysis of the CA sample and the data showed the distinctive bands linked to the vibrations of the acetate group, including the carbonyl stretching at 1750 $cm^{-1}$ (C=O), methyl bending at 1370 $cm^{-1}$ (C of —$CH_3$), and alkoxyl stretch of the ester at 1235 $cm^{-1}$ (C—O—C). The wide hydroxyl group absorption occurs at about 3400 $cm^{-1}$, the acetal connections of the cellulose backbone may be detected at around 1160 $cm^{-1}$, and the methylene asymmetric stretching occurs at 2853 $cm^{-1}$. FIG. 2C represents the FTIR spectra of CuO/MgO@HA/CA which displays bands at 657 $cm^{-1}$ and 843 $cm^{-1}$ which correspond to the broadening vibration mode for the Mg—O—Mg and the existence of Mg—O vibrations, while the single band for CuO was shown at 1556 $cm^{-1}$ because of distinctive amide I and II.

SEM

Figure 3A:
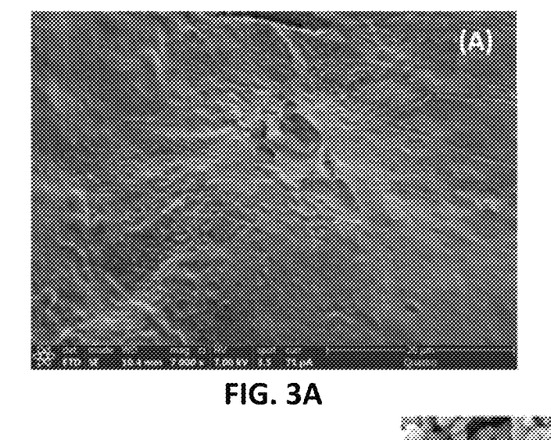
FIGS. 3A-3C are SEM images of HA (FIG. 3A), CA (FIG. 3B), and CuO/MgO@HG/CA (FIG. 3C).
Figure 3B:
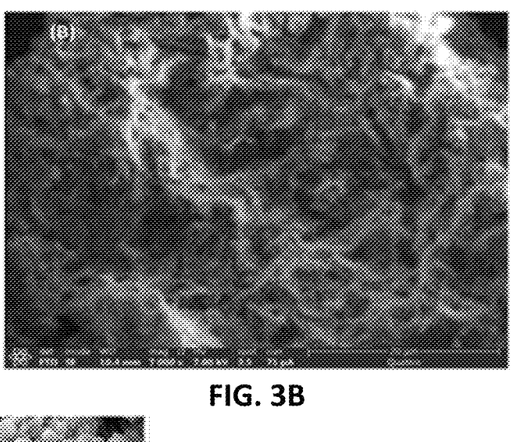
Figure 3C:
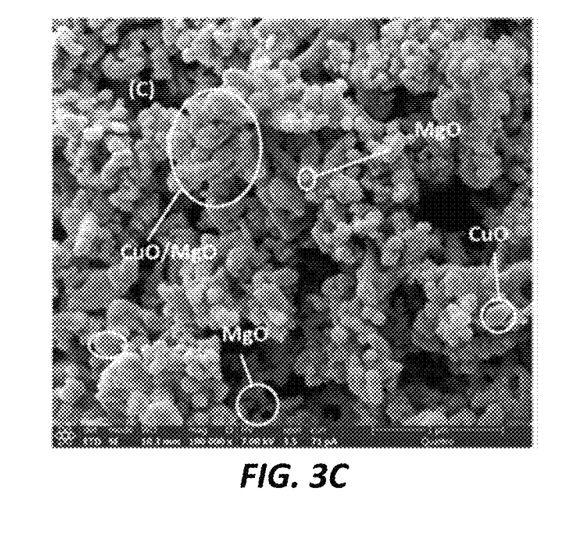

FIGS. 3A-3C display pictures of the experimental samples' scanning electron microscopy, illustrating the morphological characteristics of their surfaces. The hyaluronic acid and cellulose acetate sample's SEM image (FIGS. 3A and 3B, respectively) showed a clean surface of polymer formation. FIG. 3C shows the appearance of nanoparticles with uneven size and distribution in regions of varied densities by adding binary metal oxide nanoparticles (CuO/MgO@HA/CA). The nanoparticles of copper oxide and magnesium oxide are evenly distributed throughout the polymer mass (HA/CA).

Swelling and Contact Angle Studies

Figure 4:
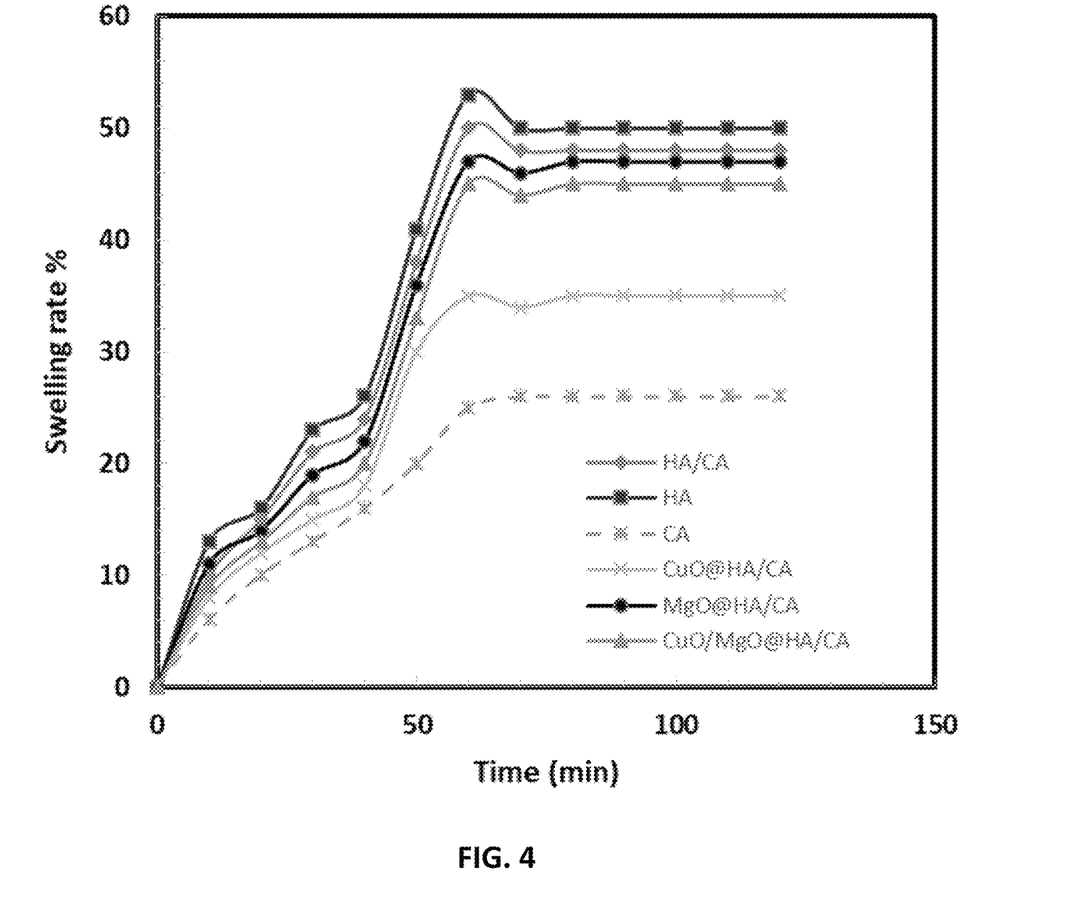
FIG. 4 shows a chart of the swelling rate percent of prepared sample nanocomposites.

FIG. 4 displays the prepared samples swelling rate and degradation behavior. The capacity of a polymer matrix to absorb and retain liquids is significantly influenced by the swelling rate. The data show that hyaluronic acid has the highest swelling rate percent, indicating that it is very hydrophilic, which causes the degree of degradation to be faster, while cellulose acetate has the lowest swelling rate percent, showing a hydrophobic property. FIG. 4 also shows that the swelling rate percent of hyaluronic acid begins to decrease when cellulose acetate is added in a ratio of 1:1. While the obtained results indicate that the swelling rate percent of the polymer mixture film decreases when adding nano-metal oxides and also when adding binary metals, the outcomes revealed that the swelling rate percent of the polymer mixture containing magnesium oxide is greater than that containing copper oxide and magnesium oxide, and the latter has a greater swelling rate percent than the polymer mixture containing coper oxide nanoparticles. This characteristic is brought about by the composite samples' porosity, which enables the collection of additional water molecules. This factor causes a more rapid rate of deterioration. By calculating the contact angle and identifying whether the sample surface is hydrophilic or hydrophobic, the hydrophilicity of the surface is further highlighted. Metal oxides are also added to the polymer mixture, which reduces its hydrophilicity and lowers the swelling rate percentage.

Figure 5:
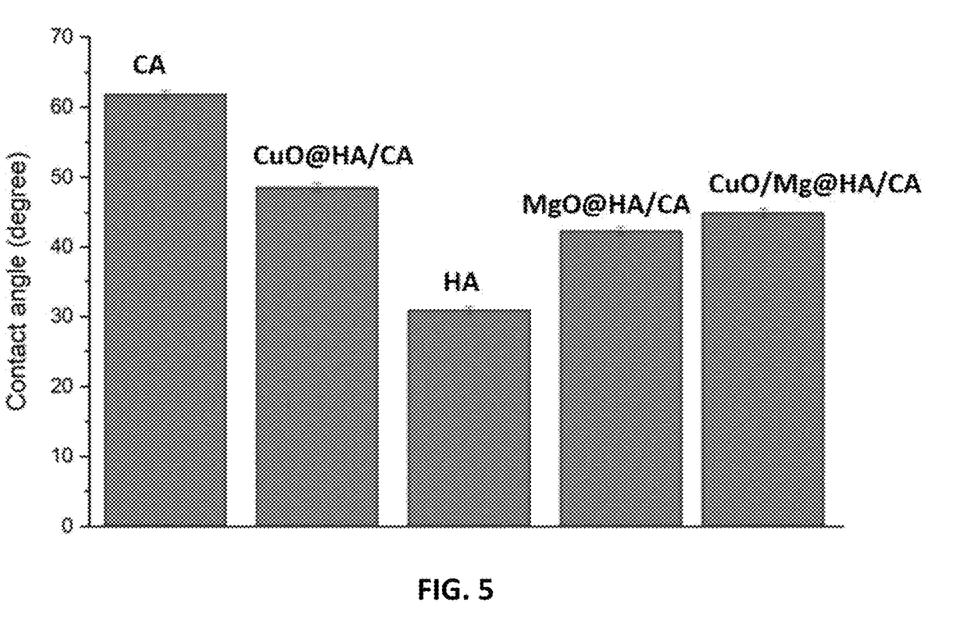
FIG. 5 shows the values of contact angles of prepared sample nanocomposites.

The functioning and biocompatibility of implanted devices are significantly influenced by the wetness of the surface, and this is determined by measuring the contact angle value, as shown in FIG. 5. As a result, a water-repellent surface (contact angle >90°) might impair cell attachment and cause the body to reject the implanted material, whereas a modest contact angle will increase cell adhesion. The samples incorporating magnesium oxide nanoparticles (MgO@HA/CA and CuO/MgO@HA/CA) showed that 30° is the lowest contact angle setting for hyaluronic acid, while the maximum contact angle was revealed for cellulose acetate. The inclusion of water-friendly surfaces as shown in FIG. 5 are beneficial for biological incorporation. It is well identified that a complicated contact angle behavior may be seen when a droplet of liquid interacts with a combination of various elements, as it is with the CuO and MgO nanoparticles. The Cassie-Baxter theory may be used analytically. FIG. 5 shows that the contact angle for CuO/MgO@HA/CA is nearly identical to that observed for MgO@HA/CA. It can therefore be inferred that MgO tiny particles cover a significant portion of the surface of CuO particles because they can readily form agglomerates, as shown by SEM analysis. In comparison to the results obtained for the MgO@HA/CA sample, this fact leads to an increase in the surface contact angle.

Degradation Performance

Figure 6:
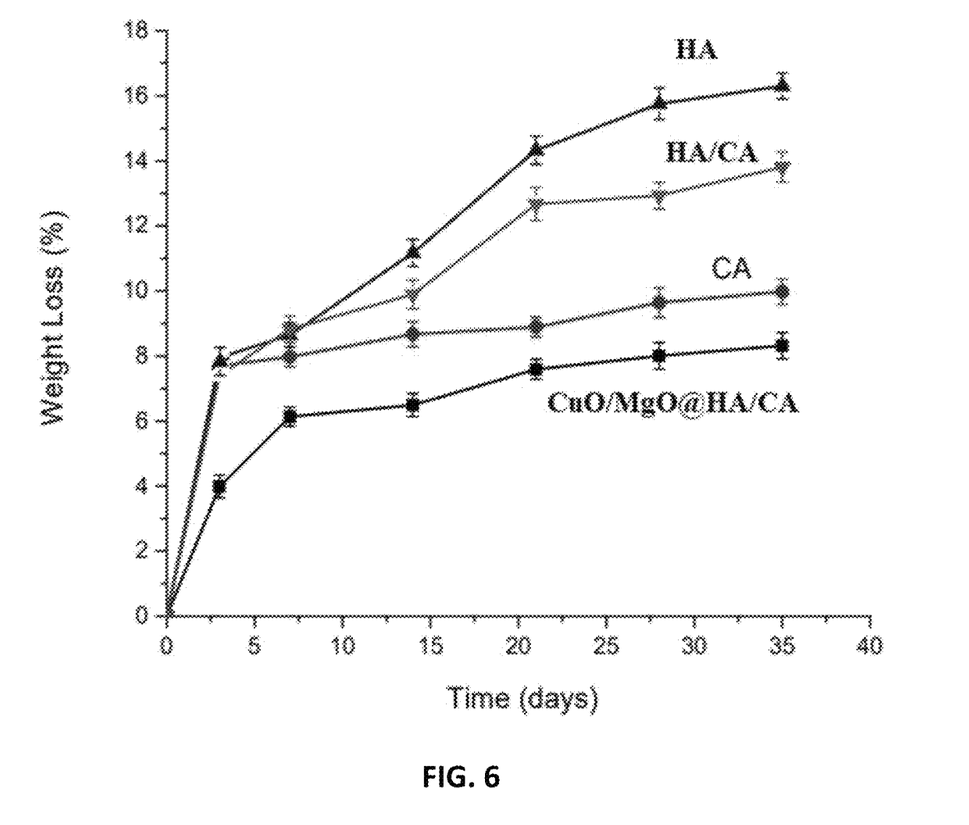
FIG. 6 shows a chart of weight loss of prepared nanocomposites after a 35-day period of immersion in PBS solution, which was used to calculate the degradation profile of prepared nanocomposites.
Figure 7A:
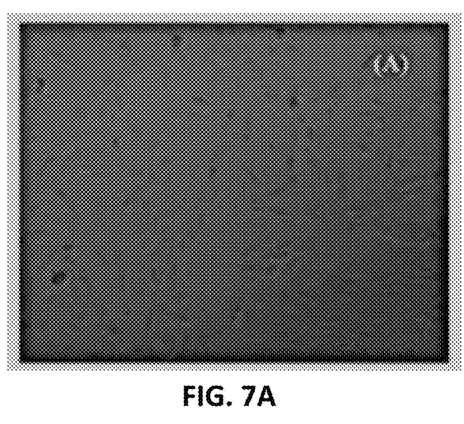
FIGS. 7A-7D are photos taken under an optical microscope of the MG-63 cell line in direct contact with a control after 24 h (FIG. 7A) or 72h (FIG. 7B), in direct contact with the CuO/MgO/@HA/CA sample after 24 h (FIG. 7C), and in direct contact with the CuO/MgO/@HA/CA sample after 72 h (FIG. 7D).
Figure 7B:
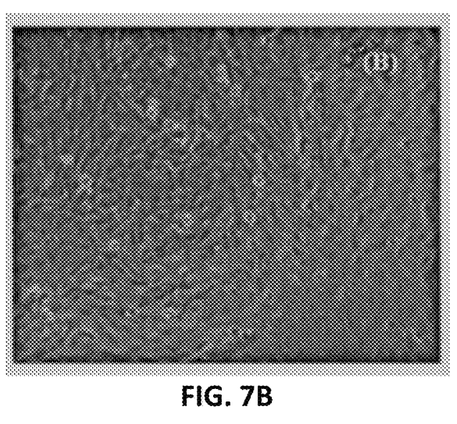
Figure 7C:
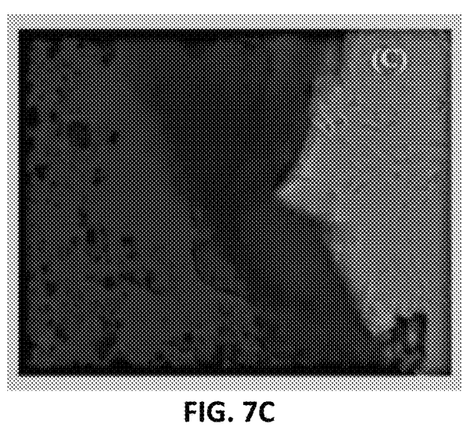
Figure 7D:
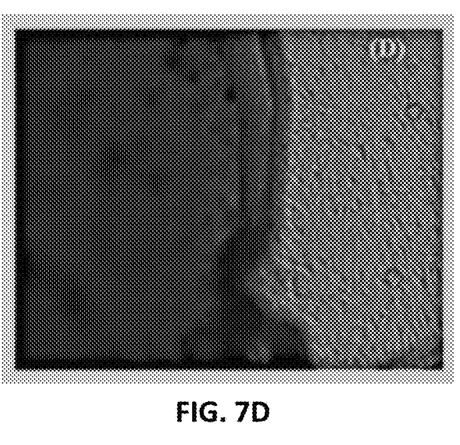

By calculating weight loss, the degradation behavior of the prepared nanocomposites was assessed. FIG. 6 depicts the progression of weight loss measured after 35 days of PBS exposure. The rate of degradation increased most quickly during the first three days of immersion in each sample. The CA and CuO/MgO@HA/CA samples exhibit lower rates of deterioration throughout the ensuing intervals, with the rise being less and more gradual. The weight loss recorded was approximately 16% for the HA sample and 13% for the HA/CA, the deterioration effectively doubling after the first three days of dipping. The sample containing a mixture of metal oxide nanoparticles (CuO/MgO@HA/CA) exhibits a lower weight loss value when compared to HA, HA/CA, and CA samples, demonstrating that the existence of the mixture of metal oxide nanoparticles reduces the degradation process. The composite samples utilized for this study's research were acquired for prevention of hyaluronic acid dressing degradation. In addition, the magnesium and coper nanoparticles are included for their potential as orthopedic materials, and particularly for use in wound dressings.

Cell Viability

Figure 8:
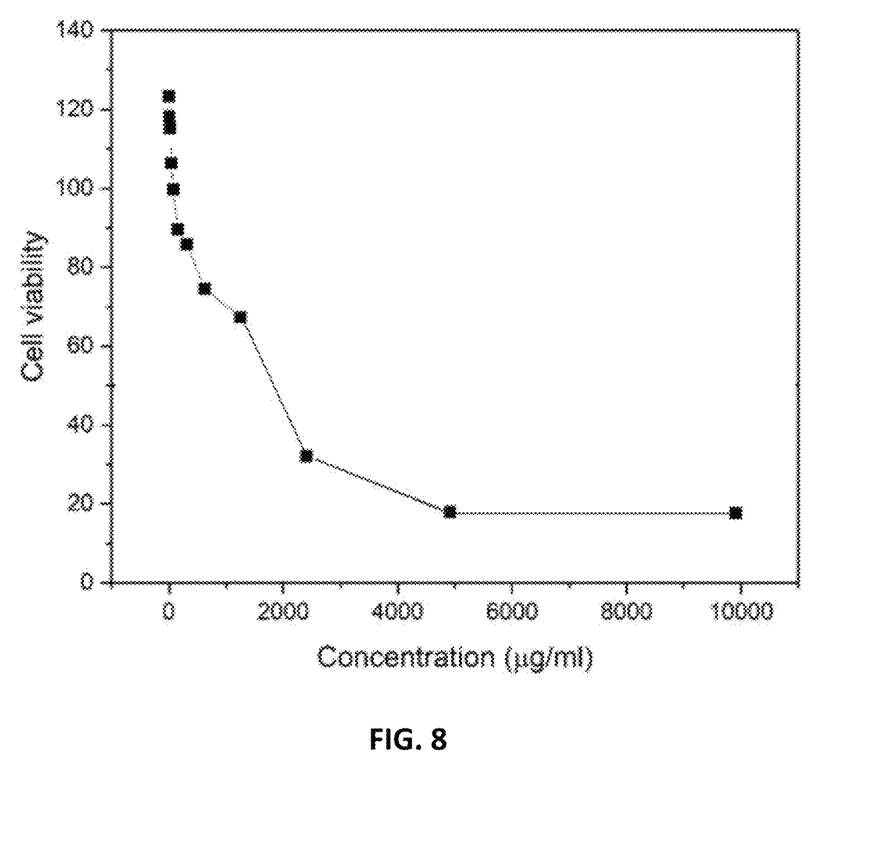
FIG. 8 is a chart of cell viability of the CuO/MgO@HA/CA scaffold after 3 days of culturing.

In terms of cell morphology and density, FIG. 7 demonstrates that when cells treated by a CuO/MgO@HA/CA sample, which implies a non-cytotoxic effect, a finding that contrasts through MTT, this has 72-hour cell viability rates between 70% and 80%. The cells that clung to the substance are likewise eliminated when an aliquot of the material is taken out before adding the MTT solution. This positive outcome shows the sample's ability to maintain cell adhesions. Furthermore, FIG. 8 displays the loaded drug's starting concentration, which was 9980.40 g/ml. With the addition of nanocomposites, the cell growth greatly enhanced and reached 122.9%, and the concentration was attained at 18.4 g/ml. Moreover, the degree of toxicity at a concentration of 50% was assessed owing to IC50 that was detected at 1810.7 g/ml. These findings may encourage cell growth and increase the scaffold's bioactivity, allowing it to be used as a wound dressing and speed up the healing process.

It is to be understood that the wound dressing based on a polymeric mixture of cellulose acetate and hyaluronic acid embedded with copper oxide and magnesium oxide nanoparticles is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for making a wound dressing, the method comprising:
    combining hyaluronic acid and deionized water to form a first mixture;
    combining cellulose acetate and acetone to form a second mixture;
    combining the first and second mixtures to form a third mixture of hyaluronic acid, cellulose acetate, deionized water, and acetone;
    separately adding at least one of a copper acetate solution and a magnesium chloride solution to the third mixture to form a fourth mixture;
    adding sodium hydride to the fourth mixture under an ultrasonic bath to form a final mixture; and
    drying the final mixture to form a film used as the wound dressing;
    wherein the ratio of hyaluronic acid to deionized water in the first mixture is about 1:10 (g/mL);
    wherein the ratio of cellulose acetate to acetone in the second mixture is about 1:10 (g/mL).

2. The method of making a wound dressing according to claim 1, wherein the ultrasonic bath lasts for a minimum of 30 minutes.

3. The method of making a wound dressing according to claim 1, wherein the third mixture is stirred until a clear solution is obtained.

4. The method of making a wound dressing according to claim 1, wherein both the copper acetate solution and the magnesium chloride solution are added to the third mixture to form the fourth mixture.

* * * * *